United States Patent [19]

Wand et al.

[11] Patent Number: 5,753,139

[45] Date of Patent: May 19, 1998

[54] HIGH CONTRAST DISTORTED HELIX EFFECT ELECTRO-OPTIC DEVICES AND TIGHT FERROELECTRIC PITCH FERROELECTRIC PITCH FERROELECTRIC LIQUID CRYSTAL COMPOSITIONS USEFUL THEREIN

[75] Inventors: Michael D. Wand; Rohini T. Vohra, both of Boulder, Colo.

[73] Assignee: Displaytech, Inc., Boulder, Colo.

[21] Appl. No.: 452,438

[22] Filed: May 26, 1995

Related U.S. Application Data

[60] Division of Ser. No. 832,414, Feb. 7, 1992, Pat. No. 5,539,555, and a continuation-in-part of Ser. No. 763,134, Sep. 20, 1991, Pat. No. 5,380,460, which is a division of Ser. No. 556,656, Jul. 20, 1990, Pat. No. 5,130,048.

[51] Int. Cl.⁶ ............ C09K 19/52; C09K 19/34; C09K 19/30
[52] U.S. Cl. ............ 252/299.01; 252/299.2; 252/299.61; 252/299.63; 252/299.66; 252/299.67
[58] Field of Search ............ 252/299.01, 299.2, 252/299.61, 299.63, 299.66, 299.67; 428/1

[56] References Cited

U.S. PATENT DOCUMENTS

| | | | |
|---|---|---|---|
| 4,722,594 | 2/1988 | Crossland et al. | 359/98 |
| 4,783,148 | 11/1988 | Tsuboyama et al. | 350/341 |
| 4,799,775 | 1/1989 | Crossland et al. | 359/98 |
| 4,852,978 | 8/1989 | Davey et al. | 359/100 |
| 5,046,830 | 9/1991 | Nakanowatori | 359/101 |
| 5,051,506 | 9/1991 | Wand et al. | 359/102 |
| 5,061,047 | 10/1991 | Bradshaw et al. | 359/101 |
| 5,109,295 | 4/1992 | Sato et al. | 359/100 |
| 5,168,381 | 12/1992 | Walba et al. | 359/100 |
| 5,380,460 | 1/1995 | Wand et al. | 252/299.6 |

FOREIGN PATENT DOCUMENTS

| | | |
|---|---|---|
| 309774 | 4/1989 | European Pat. Off. |
| 339414 | 7/1989 | European Pat. Off. |
| 404081 | 12/1990 | European Pat. Off. |
| 405346 | 1/1991 | European Pat. Off. |
| 87/06021 | 10/1987 | WIPO |

OTHER PUBLICATIONS

Armitage, D. (1991) Mol. Cryst. Liq. Cryst. 199:97–100.
Armitage, D. (1990) Proceedings of SPIE—The International Society for Optical Engineering 1257:116–124.
Funfschilling, J. and Schadt, M. (1989) J. Appl. Phys. 66(8): 3877–3882.

*Primary Examiner*—Shean C. Wu
*Attorney, Agent, or Firm*—Greenlee, Winner and Sullivan, P.C.

[57] ABSTRACT

Ferroelectric Liquid Crystals (FLCs) which exhibit a ferroelectric phase and a chiral nematic phase at temperatures above the ferroelectric phase are provided. The natural helix pitch of the FLC in the ferroelectric phase of these materials is sufficiently tighter than the thickness of the FLC layer such that it is not surface-stabilized. The chiral nematic phase has a natural helix pitch sufficiently greater than the cell thickness to facilitate alignment of the FLC in an FLC device to achieve high contrast. The FLCs of this invention are useful in making fast response, high contrast FLC electro-optic devices in which the FLC retains a helical director structure stable to unwinding.

36 Claims, 4 Drawing Sheets

HIGH CONTRAST DISTORTED HELIX EFFECT ELECTRO-OPTIC DEVICES AND TIGHT FERROELECTRIC PITCH FERROELECTRIC PITCH FERROELECTRIC LIQUID CRYSTAL COMPOSITIONS USEFUL THEREIN

CROSS-REFERENCE TO RELATED APPLICATIONS

This is a division of Ser. No. 07/832,414 filed Feb. 7, 1992 now U.S. Pat. No. 5,539,555 and a continuation-in-part of U.S. Ser. No. 07/763,134, filed Sep. 20, 1991, now U.S. Pat. No. 5,380,460, which is a division of U.S. Ser. No. 07/556,656, filed Jul. 20, 1990, now U.S. Pat. No. 5,130,048, both of which are incorporated by reference in their entirety herein.

This invention was made with partial support of the United States Government under Small Business Innovation Research grant numbers F19628-85-C-0087 and F33615-87-C-5293 from the U.S. Air Force. The United States Government has certain rights in this invention.

FIELD OF THE INVENTION

This invention relates to electro-optic devices which contain ferroelectric liquid crystals (FLCs). In particular, the devices of the present invention are non-surface stabilized FLC cells in which the FLC has tight pitch in the ferroelectric phase, for example, Distorted Helix Ferroelectric (DHF) devices. Chiral nonracemic FLC compositions of this invention exhibit a tight pitch helix in the ferroelectric phase and a long pitch helix in the chiral nematic phase.

BACKGROUND OF THE INVENTION

Lagerwall and Clark described the surface-stabilized ferroelectric liquid crystal (SSFLC) effect and its application to electro-optic shutters and display devices (U.S. Pat. Nos. 4,367,924 and 4,563,059). In SSFLC cells, the FLC is aligned between transparent electrodes in the so called "bookshelf" alignment in which the smectic layers are substantially perpendicular to the electrodes and the long axis of the FLC molecules is parallel to the electrodes. In this configuration, the natural helix typically formed in the ferroelectric phase is suppressed by surface interactions in the cell. Suppression of the helix results in a bistable cell in which the optic axis of the cell can be rotated in the plane of the electrodes by 2Θ, where Θ is the tilt angle, by changing the sign of the applied driving voltage. Tilt angle is an intrinsic property of a FLC. In order to suppress the helix, the cell thickness (d) must be comparable to or smaller than the magnitude of the pitch of the helix. Thus, for applications in the visible in which cell thicknesses of 0.5–6 µm are most useful (assuming a birefringence of 0.15–0.3), the chiral tilted smectic ferroelectric natural helix pitch in the FLC should be longer than 0.5–10 µm.

Electro-optic effects in FLC cells in which the helix in the smectic C* phase is not suppressed by surface-stabilization have also been described. The Distorted Helix Ferroelectric (DHF) effect, described for example in Ostovski et al., Advances in Liquid Crystal Research and Applications, Oxford/Budapest, (1980) page 469 and in Funfschilling and Schadt (1989) J. Appl. Phys. 66(8):3877–3882), is observed in FLCs aligned between electrode plates in which the natural helix pitch in the smectic C* (or other chiral tilted smectic ferroelectric) phase is sufficiently tight, i.e., shorter than the FLC cell thickness (d), so that the helix is not suppressed. DHFLC electro-optic devices have an FLC aligned between electrode plates. Most typically the FLC is planar aligned and in the "bookshelf" geometry. A driving voltage applied to the electrodes to generate an electric field across the FLC layer. Unlike, surface-stabilized FLC devices, the natural helix of the aligned chiral smectic phase is present in the aligned FLC material in the DHF effect device. The helix forms parallel to the plates and perpendicular to the smectic layers as illustrated in FIG. 1. The magnitude of the pitch of the helix is the distance along the helix axis for one full turn of the helix and the sign of the pitch (+ or −) represents the direction of twist of the helix. The term "tight" pitch, which can be a positive or negative value, is associated with shorter axial lengths for one full turn of the helix. The term "pitch" as used herein refers to the magnitude of the pitch; the terms "sign of the pitch" or "twistk" refer to the direction of twist of the helix.

SSFLC and DHF cells can be operated in reflection mode in which one of the electrode plates is reflective (see, for example, U.S. Pat. No. 4,799,776).

When the magnitude of the smectic C* helical pitch is comparable to the wavelength of visible light, a striped pattern appears in the device and in effect a diffraction grating is formed. If the magnitude of the pitch is less than the wavelength of light (and preferably less than ½λ of light), light diffraction is minimized and the apparent refractive index of the FLC is the average over many director orientation of the helix as shown in FIG. 1. In the field-free state with zero applied electric field and with no surface stabilization, the smectic C* helix is in its natural state.

The molecular director, ñ, makes an angle, Θ, with the layer normal. In the field-free (E=0) state, due to the presence of the helix, averaging occurs and the apparent optic axis of the DHFLC coincides with the helix axis, as shown in FIG. 1.

If the voltage applied across the FLC layer is above a certain critical level $E_c$, the helix is completely unwound forming two distinct optical states, as in an SSFLC device. Application of a voltage below $E_c$ deforms the helix, generating an effective rotation of the optic axis of the DHFLC. The orientation of the optic axis of the DHFLC layer can be changed in a continuous fashion proportional to the applied electric field changing the optical anisotropy of the FLC. DHF cells display rotation of their optic axis that is dependent on the magnitude of the applied electric field and also exhibit a change in apparent birefringence (Δn) as a function of the magnitude of the applied electric field.

The maximum field-induced angle of rotation of the optic axis of the DHFLC is Θ, the tilt angle of the material. A maximum field induced optic axis rotation of 2Θ can be obtained by application of a +/− voltage step, $+/-E_{max}$, where $E_{max}$ is the minimum voltage required to obtain a rotation of Θ and the magnitude of $E_{max}$ is less than $E_c$.

DHF-effect cells typically exhibit significantly lower apparent refractive index than SSFLC cells due to the averaging noted above. Thus, for a given desired optical retardation, DHF cells are typically thicker than comparable SSFLC cells. Birefringence for DHFLC cells typically ranges from about 0.06 to 0.13, about ½ that of SSFLC cells. DHFLC waveplates are as a consequence, typically, thicker than comparable SSFLC waveplates. High birefringence materials are useful in DHF applications to minimize cell thicknesses.

$E_c$ is inversely proportional to the spontaneous polarization of the FLC and the ferroelectric phase pitch, having the relationship:

$$E_c P_s \propto \left(\frac{1}{p^2}\right)$$

Thus, the higher the spontaneous polarization and longer the pitch, the lower the voltage necessary to control the effect. Response time ($\tau$) for the DHFLC cell is defined as:

$$\tau \propto \gamma \frac{p^2}{\theta^2}$$

where $\gamma$ is the orientational viscosity and $\theta$ is the tilt angle. Increasing $P_s$ lowers the threshold voltage, but does not increase the speed, while tightening the pitch increases both the speed and $E_c$. By increasing both $P_S$ and decreasing p, the response speed can be significantly increased while maintaining a low threshold voltage. Decreasing the viscosity also improves the response time.

EP Application 309,774 refers to DHFLC display cells with chiral smectic FLCs whose helical structure can be changed by an electric field to alter the optical anisotropy of the cells. The application refers to DHF cells in which the ratio of the cell thickness to the helix pitch of the FLC (d/p) is more than 5 and preferably more than 10, in which $\Theta$ is between 22.5° and 50° and in which a so-called phase factor:

$$\frac{d\theta_0^2 \Delta n}{\lambda}$$

is apparently constrained to be greater than 0.1, and preferred to be greater than 0.45. This requirement imposes limits on cell thicknesses which can limit the applications of the DHFLC devices. The application refers to FLC mixtures of 5-alkyl-2-(p-alkoxyphenyl)pyrimidines and a chiral non-racemic terphenyl diester. See also EP application 339,414.

EP application 405,346 refers to bistable FLC cells having aligned FLCs with an achiral smectic C host mixture and a dopant which induces a pitch less than 1 µm. The mixtures are referred to as having spontaneous polarization greater than 10 nC/cm² and $\theta$ greater than 10°. The described cell displays dark parallel lines at zero voltage between crossed polarizers indicating a non-homogeneous structure.

EP application 404,081 refers to FLC elements having high polarization and tight pitch. This application refers to the use of tight C* pitch materials, where p is at least less than ½d, in SSFLC cells to eliminate optical hysteresis that is observed in cells having high spontaneous polarization. Mixtures having C* pitch in the range 0.25 µm to 0.63 µm were reported, but of these the tightest pitch at room temperature was about 0.39 µm. The tight C* pitch FLC mixtures were reported to have N* pitch at least greater than 8 µm.

Funfshilling and Schadt (1989) J. Appl. Phys. 66(8) :3877–3882 refer to fast response, multiplexible DHFLC displays. The authors report that DHF cells require both very short pitch FLCs, with pitch much shorter than cell thickness, and weak surface interactions in the cell. Several methods of cell preparation are reported to decrease the tendency of the helix to unwind: application of shear, the use of different rubbing directions on top and bottom cell plates and surface treatments that lead to zig-zag defects in SSFLCs. These treatments, however, have a detrimental effect on the optical contrast of the cell. They report DHF cells produced by uni-directional rubbing of alignment layers with contrast ratio (ON/OFF) of 12:1 and DHF cells of sheared cells of 40:1. Thus, the production of high contrast DHFLC electro-optic devices is problematic.

SUMMARY OF THE INVENTION

It is an object of this invention to provide fast response, high contrast FLC electro-optic devices in which the FLC retains a helical director structure which is stable to unwinding. It is a particular object of this invention to provide fast response, high contrast DHFLC electro-optic devices which are stable to unwinding. It is also an object of this invention to provide FLC compositions with liquid crystal phase properties, tight ferroelectric phase pitch, long N* pitch and high spontaneous polarization that are useful in FLC electro-optic devices requiring tight ferroelectric pitch and particularly useful in FLC electro-optic devices which require the presence of a helical director structure in the FLC.

It is a further object of this invention to provide fast response, high contrast DHFLC cells which are half-wave plates, particlarly those useful in the visible wavelength region, in which the FLCs are stable to unwinding.

To further these objects, the present invention provides high contrast electro-optic devices containing non-surface stabilized FLC cells which retain a helical director (fi structure and exhibit a change in optical anisotropy as a function of the magnitude of an applied electric field or driving voltage. In particular, the present invention provides high contrast DHF-effect cells. The FLC cells of this invention incorporate chiral ferroelectric liquid crystals which exhibit a ferroelectric phase, for example a smectic C* phase, and a chiral nematic (N*) phase at temperatures above the ferroelectric phase. The FLC cells of the present invention comprise uniformly spaced electrode-containing plates between which the FLC is aligned. At least one of the electrode plates are transparent or semi-transparent. One of the electrode plates may be reflective, producing a DHF cell which operates in reflection mode. The cell is provided with a means for detecting the change in optical anisotropy in the FLC induced by the application of the electric field, for example, in a transmission-mode cell, an entrance polarizer and a polarization analyzer can be provided on either side of the electrode plates.

A means for aligning the FLC can be provided within the cell, for example on the inside surfaces of the electrode plates in contact with the FLC. The means for aligning can be an alignment layer which is subjected to uni-directional, parallel or antiparallel rubbing or brushing prior to introduction of the FLC between the plates. For example, nylon, polymide or polyamide layers can be deposited or spun onto the plates. Oblique deposition of SiO cells is an alternative alignment means. Rubbed nylon alignment layers are preferred for production of high contrast DHFLC cells.

The FLC layers of the devices of the present invention are preferably planar aligned and most preferably aligned in the "bookshelf" geometry. In the FLC devices of the present invention, the natural helix pitch of the FLC in the ferroelectric phase is sufficiently tighter than the thickness of the ferroelectric liquid crystal layer, i.e., the FLC cell thickness (d), such that the ferroelectric liquid crystal layer in the device exhibits a helical director structure and thus is not surface-stabilized. In the N* phase of the FLCs, the natural helix pitch is sufficiently greater than the cell thickness to facilitate alignment of the FLC in the device such that it displays high optical contrast of at least about 40:1, and more preferably 100:1 or more. To further facilitate good alignment, it is desirable that the FLC also have an orthogonal smectic phase intermediate in temperature between the ferroelectric and the N* phases. Orthogonal smectic phases include smectic A and smectic B phases, among others. The presence of a smectic A phase is preferred.

High contrast electro-optic devices of this invention preferably comprise FLC materials wherein the magnitude of natural helix pitch in the ferroelectric phase is less than about ⅕d (the FLC cell thickness) and the magnitude of the natural helix pitch in the N* phase is at least about equal to d. It is more desirable that the magnitude of the natural pitch in the ferroelectric phase is less than about ¹⁄₁₀d. The natural helix pitch in the N* phase is preferably longer than about 4d and more preferably longer than about 8d.

It is preferred that the FLCs of this invention exhibit ferroelectric phases with the desired pitch properties at useful device operating temperatures. Useful operating temperatures for an FLC or DHFLC device are dependent on the desired application of the device. In some cases, room temperature (20°–30° C.) or lower (10°–30° C.) operation will be desired. In other cases, e.g., projection devices, higher operating temperatures (50°–80° C.) will be desirable. Useful operating temperatures for devices of the present invention, thus, range from about 10° C. to about 80° C. The FLCs of this invention preferably exhibit the desired long N* pitch properties up to about 1°–2° C. above the transition temperature into the N* phase. More preferably the FLCs of this invention display the desired long N* pitch at least up to about 5° C. above the N* transition point. Most preferably, the FLCs of this invention display the desired long N* pitch over the entire N* phase.

Ferroelectric phases of this invention are chiral tilted smectic phases, including smectic C*, I*, F*, H*, J*, and G*, all of which have exhibited ferroelectric properties (Meyer et al. (1975) J. de Physique 36, L-69). The preferred ferroelectric phase of the FLCs of the present invention is a smectic C* phase.

Orthogonal smectic phases of this invention are those in which the long molecular axis of the FLC compounds is on the average perpendicular to the smectic layers, including smectic A and B phases.

For use in the visible wavelength region, FLC cell thicknesses between about 0.5 to 6.0 μm, dependent on the birefringence of the FLC, are preferred. To avoid diffraction and surface-stabilization effects, in DHFLC device applications in the visible, it is preferred that the natural helix pitch of the FLC in the ferroelectric phase be substantially less than the wavelength of light to be used, and substantially less than the cell thickness. Pitch in the ferroelectric phase having a magnitude ranging from less than 0.1 to 1.2 μm is desirable. Ferroelectric phase pitch of magnitude less than about 0.25 μm is more desirable and magnitude less than about 0.15 μm is most desirable. In such cells, natural N* pitch of a magnitude greater than 4d is desirable and a magnitude greater than 8d is more desirable. The preferred ferroelectric phase is the smectic C* phase. Again it is preferred for DHFLC devices useful in the visible that the FLCs of the device exhibit the desired ferroelectric phase and pitch at useful operating temperatures and exhibit the N* pitch up to at least about 5° C. above the transition into the N* phase. It is also preferred that the FLCs have a smectic A phase between a smectic C* and the chiral nematic phases.

To achieve the high contrast devices of the present invention, particularly high contrast DHFLC devices, FLC compositions which comprise at least two components and which exhibit a ferroelectric phase and a N* phase at temperatures above the ferroelectric phase, wherein the natural helix pitch in the ferroelectric phase is less than about ⅕d, preferably less than about ¹⁄₁₀d, and the natural helix pitch in the chiral nematic phase is equal to or greater than d, preferably greater than 4d, and more preferably greater than 8d, are provided. Preferred compositions are those having a smectic C* ferroelectric phase.

FLC compositions of this invention comprise a chiral dopant which induces a tight natural helix pitch in the ferroelectric phase, but does not induce a tight helix pitch in the chiral nematic phase of a FLC composition. FLC compositions of this invention further comprise a host material which itself possesses a tilted smectic phase and may be chiral or achiral. Hosts most preferably have a nematic phase at temperatures higher than the tilted smectic phase and preferably also have an orthogonal smectic phase intermediate in temperature between the tilted smectic and nematic phase. In the FLC composition, the natural helix pitch in the N* phase is at least 4-fold longer than that in the ferroelectric phase, and preferably is 10-fold longer. The FLC compositions may contain more than one tight pitch-inducing chiral dopant, preferably all of which have the same sign of ferroelectric phase pitch. To maximize N* pitch, it is desirable that not all of the chiral dopants combined in an FLC compositions have the same sign of N* pitch. Hosts may be and most often are mixtures of components. Hosts are typically achiral, but may be chiral nonracemic FLCs having a low spontaneous polarization. If a chiral nonracemic FLC host is employed, it is preferred that the FLC host and the tight pitch-inducing FLC dopants that are combined have the same sign of ferroelectric pitch.

Preferred FLC compositions of this invention exhibit the phase sequence: I, N*, orthogonal smectic, ferroelectric, X (where I is isotropic, N* is chiral nematic and X is crystalline) with decreasing temperature. More preferred FLC compositions exhibit the phase sequence I, N*, A, C*, X (where I=isotropic, N*=chiral nematic, A=smectic A, C*=smectic C*, and X=crystalline) with decreasing temperature.

The FLC compositions of the present invention may also contain a nematic phase pitch compensation agent or mixture of such agents all of which preferably exhibit the opposite sign of N* pitch (i.e., direction of helix twist) as the mixture of the FLC host and tight pitch-inducing FLC dopant.

Preferred FLC compositions of the present invention contain less than about 30% by weight of tight pitch-inducing chiral dopant components and less than about 5–10% by weight of nematic pitch-compensation agents. More preferred compositions contain less than about 20% by weight of tight pitch-inducing dopants. More preferred compositions contain less than about 1% by weight of nematic pitch-compensation agents.

In preferred FLC compositions of the present invention, the magnitude of the spontaneous polarization is greater than about 10 nC/cm². Preferred FLC compositions have tilt angles of greater than about 10°, more preferably greater than about 18° and most preferably greater than or equal to 22.5°.

Generally preferred chiral dopants of the present invention are chiral nonracemic compounds having a liquid crystal core, a second tail group, and a substituted 2,3-dihaloalkyloxy chiral tail of the formula:

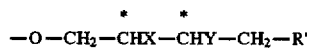

where * represents an asymmetric carbon, X and Y are, independently of one another, halogens and R' is a group having from one to about twenty carbon atoms in which one or more nonneighboring carbon atoms can be replaced with a double bond, an O atom, a S atom or a Si(CH$_3$)$_2$ group or R' is an acyl group—OCO—RΔ where R" is a group having from two to about twenty carbon atoms and wherein one or more non-neighboring carbon atoms can be replaced with a double bond, an O atom, a S atom or a Si(CH$_3$)$_2$ group. R' can contain straight-chain or branched alkyl or alkenyl portions as well as cycloalkyl or cycloalkenyl portions. Preferred chiral dopants are those in which X and Y are, independently of one another, F or Cl, and more preferred FLC dopants are those in which X and Y are both F. In general, the liquid crystal core of the chiral dopant can be any mesomorphic group, for example, those containing aromatic or cyclohexyl groups, which is compatible with tight pitch induction. Two and three ring cores are preferred. The second tail group can generally be chiral or achiral and typically contains from one to about twenty carbon atoms and can be, among others, a straight-chain or branched alkyl, alkene, cycloalkyl, cycloalkenyl, ether, ester, acyl, thioether, thioester or an alkylsilyl group.

In specific embodiments, tight pitch-inducing chiral dopants of the present invention are chiral nonracemic compounds having the formula:

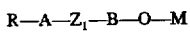

wherein A and B, independently of one another, can be selected from 1,4-phenylene, 1,4-phenylene in which one or two of the ring carbon atoms are replaced with nitrogen atoms, or 1,4-cyclohexylene and Z$_1$, is a single bond, a —CO—O— or —O—CO— group or an O atom when one of A or B is a 1,4-cyclohexylene group. For example, —A—Z$_1$—B— can include:

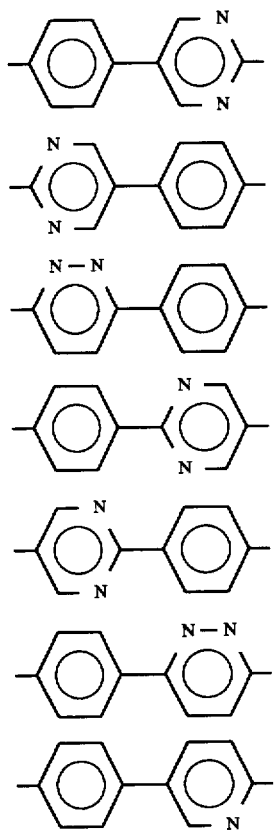

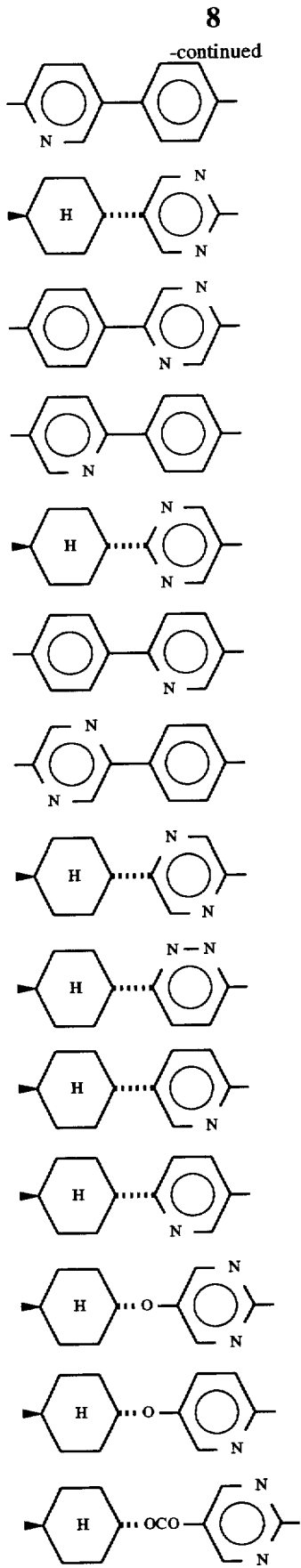

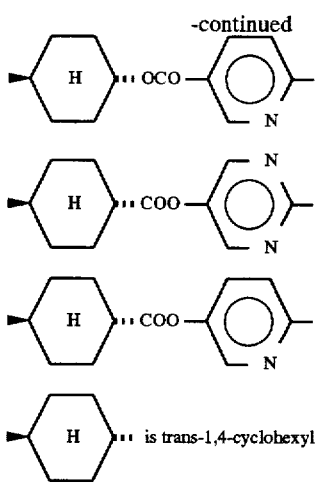

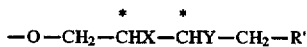

R is a group having from one to twenty carbon atoms in which one or more non-neighboring carbon atoms can be replaced with a double bond, an O atom, a S atom or a Si(CH$_3$)$_2$ group; R can include straight-chain or branched alkyl, alkenyl, cycloalkyl, or cycloalkenyl portions, and O—M is a 2,3-dihaloalkyloxy moiety of the formula:

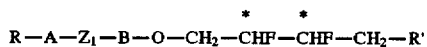

where * represents an asymmetric carbon, X and Y are, independently of one another, halogens, R' is a group having from one to about twenty carbon atoms in which one or more nonneighboring carbon atoms can be replaced with a double bond, an O atom, a S atom or a Si(CH$_3$)$_2$ group or an acyl group, —OCO—R", where R" is a group having from one to about twenty carbon atoms and wherein one or more non-neighboring carbon atoms can be replaced with a double bond, an O atom, a S atom or a Si(CH$_3$)$_2$ group. R' and R" can include straight-chain or branched alkyl, alkenyl, cycloalkyl or cycloalkenyl portions.

In other specific embodiments, tight pitch-inducing dopants of the present invention are chiral nonracemic compounds having the formula:

$$R—A—Z_1—B—O—CH_2—\overset{*}{C}HF—\overset{*}{C}HF—CH_2—R'$$

where * represents an asymmetric carbon, Z$_1$, is a single bond, B is a 1,4-phenylene and A is a 2,5-phenylpyrimidine, e.g., —A—Z$_1$—B— can be:

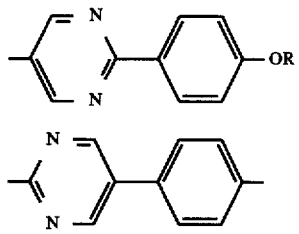

and wherein R is a group having from one to twenty carbon atoms in which one or more non-neighboring carbon atoms can be replaced with a double bond, an O atom, an S atom, a Si(CH$_3$)$_2$ group and, R' is an alkyl group having from one to about twenty carbon atoms or an acyl group —OCO—R" having from one to about twenty carbon atoms.

In specific embodiments of this invention, R' can be an alkyl group having from three to about twenty carbons, an ω-monoalkene having three to about twenty carbon atoms, an alkylsilyl group having from four to about twenty two carbon atoms or an acyl group OCO—R" wherein R" can be an alkyl group having from three to about twenty carbons, an ω-monoalkene having from three to about twenty carbon atoms, or an alkylsilyl group having from four to about twenty-two carbon atoms.

In other specific embodiments of this invention, R' can be an alkyl group having from one to about twenty carbon atoms or an acyl group OCO—R" wherein R" is an alkyl group having from one to about twenty carbon atoms. Preferred alkyl R' and R" groups have from about six to about twelve carbon atoms.

In a more specific embodiment, the core —A—Z$_1$,—B— is:

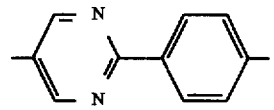

and R' is an alkyl group having from one to about twenty carbon atoms, an ω-alkene group having from two to about twenty carbon atoms, an alkylsilyl group having from four to about twenty-two carbon atoms, or an acyl group, OCO—R" in which R" can be an alkyl group having one to about twenty carbon atoms, an ω-alkene group having two to about twenty carbon atoms or an alkylsilyl group having from four to about twenty-two carbon atoms. Preferred alkyl groups for R and R' are those containing about six to twelve carbon atoms.

More preferred, in order to obtain higher spontaneous polarization FLC compositions, are chiral dopants having 2,3-difluoroalkyl tails in which the configuration of the asymmetric carbons is 2(R), 3(R) or 2(S), 3(S).

Hosts useful in the devices of the present invention comprise at least about 10% by weight of one or more dioxysubstituted compounds of the formula:

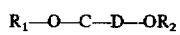

in which one of C or D is a 1,4-phenylene and the other of C or D is a 1,4-phenylene in which one or more of the carbon atoms of the ring are replaced with a nitrogen atom, and wherein R$_1$ and R$_2$ are, independently of one another, alkyl or alkenyl groups having from one to about twenty carbon atoms or an alkylsilyl group having from four to about twenty-two carbon atoms. R$_1$ and R$_2$ can contain straight-chain or branched alkyl, alkenyl, cycloalkyl or cycloalkenyl portions. Preferred hosts components of this invention are phenylpyrimidines in which one of C or D is a 1,4-phenylene and one of C or D is a 2,5-pyrimidine. In specific embodiments of this invention, R$_1$ and R$_2$ are alkyl groups or ω-monoalkenes having from one to about twenty carbon atoms or silylalky groups having a terminal Si(CH$_3$)$_3$ group having from four to about twenty-two carbon atoms. Preferred R$_1$ and R$_2$ alkyl groups have from about six to about twelve carbon atoms.

In a specific embodiment, hosts of this invention comprise at least about 10% by weight of a compound of the formula:

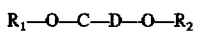

wherein C is a 2,5-pyrimidine and D is a 1,4-phenylene and wherein R$_1$ and R$_2$ are, independently of one another alkyl or ω-alkenyl groups having from three to about twenty carbon atoms.

Hosts of this invention can also comprise one or more of the compounds of the following formulas:

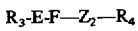

or

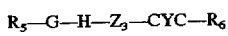

where $R_3$, $R_4$, $R_5$ and $R_6$ are, independently of one another, alkyl or alkenyl groups having from about one to about twenty carbon atoms, or an alkylsilyl group having from about four to about twenty-two carbon atoms. $R_3$, $R_4$, $R_5$ and $R_6$ groups can contain straight-chain or branched alkyl, alkenyl, cycloalkyl or cycloalkenyl portions.

One of E or F is a 1,4-phenylene and the other of E or F is a 1,4-phenylene in which one or two of the ring carbons are replaced with a nitrogen atoms and $Z_2$ is either an oxygen atom, a —CO—O— or a —O—CO— group. One of G or H is a 1,4-phenylene and the other of G or H is a 1,4-phenylene in which one or two of the ring carbons can be replaced with a nitrogen atom and $Z_3$ is a single bond, an oxygen atom, a —O—CO— group or a —CO—O— group. Cyc is a 1,4-cyclohexyl group.

—E—F— and —G—H— are preferably phenylpyrimidines, including:

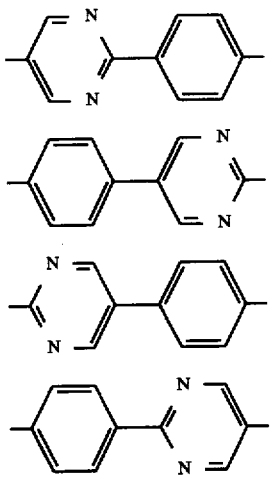

$Z_2$ is preferably an oxygen atom. $Z_3$ is preferably a single-bond or a —O—CO— group, most preferably a —O—CO— group. Cyc is preferably a trans-1,4-cyclohexyl group. $R_3$, $R_4$, $R_5$ and $R_6$ preferably are alkyl or ω-alkenyl groups having from three to about twenty carbon atoms and more preferably are alkyl groups having from about six to twelve carbon atoms.

Preferred host mixtures of this invention comprise about 50% or more by weight of compounds of formula:

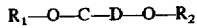

or about 50% by weight of a mixture of compounds of formulas:

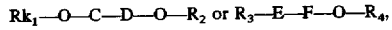

wherein at least 10% by weight is a compound of formula

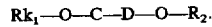

Preferred host mixtures also comprise at least about 10% by weight of compounds of formula:

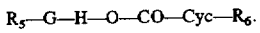

This invention also provides methods for assaying candidate chiral nonracemic compounds for their ability to induce tight ferroelectric phase pitch in mixtures which retain a long N* pitch. Analogous methods for identifying hosts suitable for use in tight ferroelectric pitch, long N* pitch mixtures of this invention are also provided.

This invention further provides methods of making high contrast DHF cells, particularly high contrast cells that are half-wave plates. Such DHF cells are prepared by introducing an FLC composition of the present invention which exhibits tight ferroelectric phase pitch at device operating temperatures and long N* pitch at temperatures at least up to 1°–2° C. above the N* transition point between uniformly-spaced electrode plates. The electrode plates are surface-treated to provide an alignment layer, such as a uni-directionally-rubbed polymer layer. The FLC is heated to at least 5° C. above the transition point into the N* phase, introduced between the surface-treated electrode plates and slowly cooled at a rate of between about 0.05°–2.0° C./minute into the ferroelectric phase to achieve good alignment of the FLC.

FLC compositions of this invention can be employed in any FLC device requiring or benefiting from the use of a tight ferroelectric phase pitch material. The FLC compositions of this invention can be employed in antiferroelectric-effect electro-optic devices and in bistable SSFLC-like cells. This invention also provides FLC devices which have FLC layers which comprise the FLC compositions of this invention.

BRIEF DESCRIPTION OF THE FIGURES

The change in C* (open squares) and N* pitch (closed squares) in microns as a function of temperature (°C.) is shown. The scale for N* pitch (y-axis, right) is ten-fold larger than that for C* pitch (y-axis, left). The temperature ranges of the smectic A (A), smectic C* (C*), chiral nematic (N*) and isotropic (I) phases are indicated on the graph with transition points indicated by dashed lines. The actual values of C* pitch and N* pitch in Mixture 1 are both negative. In FIG. 4, the absolute magnitudes of pitch are used in order to compare the variation in the magnitude of the pitch as a function of temperature.

DETAILED DESCRIPTION OF THE INVENTION

Figure 1:
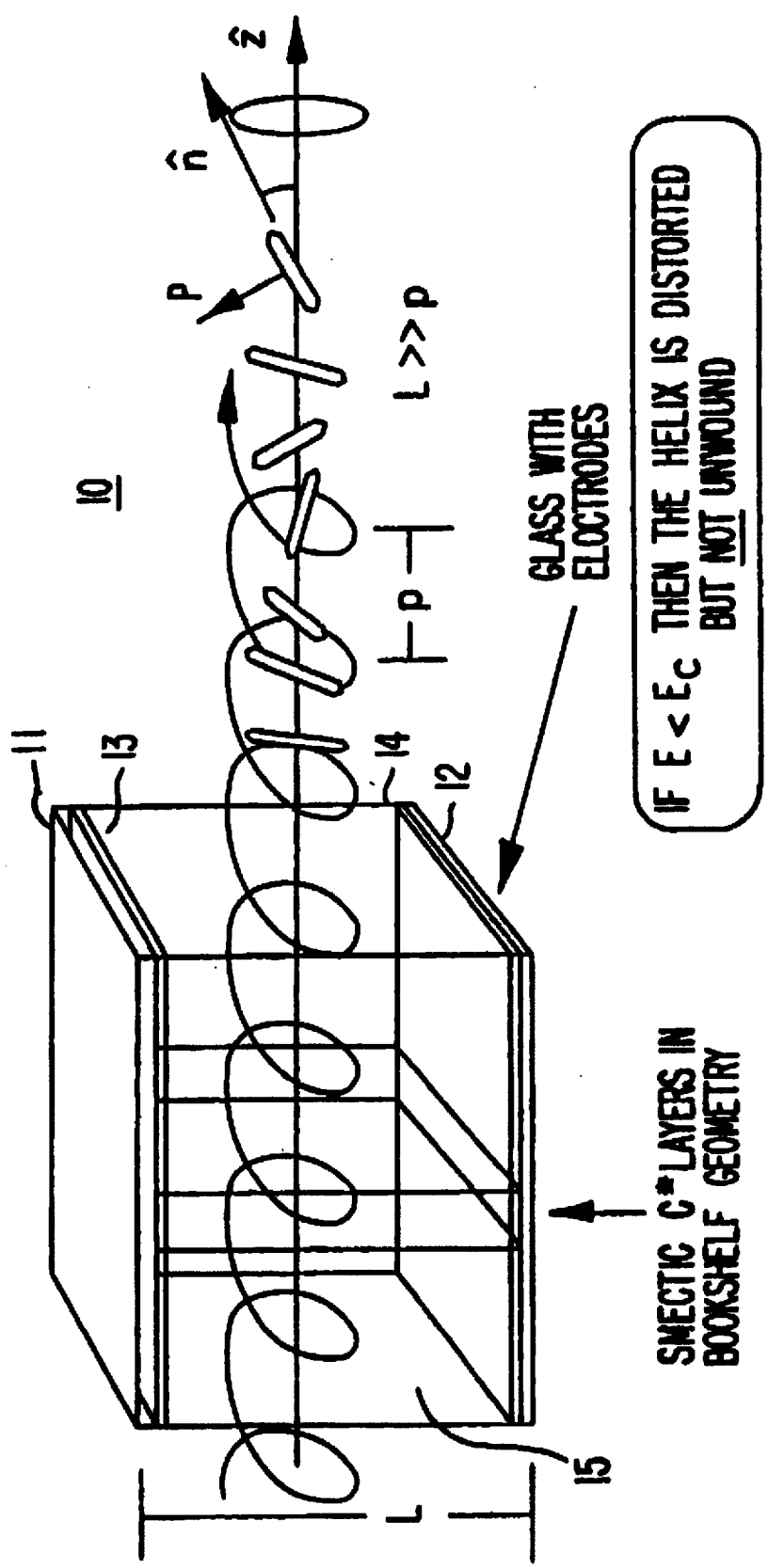
FIG. 1 is a schematic representation of a DHFLC cell with smectic C* layers perpendicular to the electrode plates in the bookshelf geometry. The helix axis is along fi, the smectic layer normal, parallel to the electrode plates. The pitch of the helix (p) is illustrated. For DHF-effect cells the cell thickness (d) is much greater that the magnitude of the C* pitch.

It is well-known in the art that improved alignment and contrast ratio in SSFLC cells can be facilitated by an FLC having a long pitch N* phase at higher temperatures to the ferroelectric tilted chiral smectic phase (see for example WO 87/06021). To facilitate alignment in SSFLCs, N* pitch should be at least equal to d, and preferably 4d or more. It is also well-known in the art for the preparation of SSFLC cells that cell alignment is further facilitated by the presence in the FLC of a smectic A phase intermediate in temperature between the chiral tilted smectic ferroelectric phase and the N* phase. SSFLC cells, however, have been considered in the art to require relatively long pitch (typically longer than d and preferably longer than 4d) in their ferroelectric phase.

It has been difficult, with prior art methods and compositions to obtain high contrast in DHFLC devices. The contrast ratio is defined as the ratio of the transmitted light in an ON (maximal white light transmitted through the device) and an OFF (minimal white light transmitted through the device) state. To achieve maximum contrast, a DHFLC cell half-wave plate is positioned between crossed (linear) polarizers and oriented such that when $E_{max}$ (or $-E_{max}$) is applied a minimum transmission is observed. Maximum contrast is obtained when the voltage step applied across the cell rotates the optic axis by a total of 450 between the OFF and the ON state. Most often contrast is limited by light leaking through in the OFF state. In addition, the maximum transmission in the ON state is limited by a maximum total optic axis rotation less than 45°, since FLCs often have tilt angles less than 22.5°.

Minimal transmission in the OFF state requires good uniform alignment of the DHFLC within the cells between the electrode plates. Very little has been reported in the prior art about improving alignment in DHFLC cells. Funfschilling and Schadt (1989) supra suggest that the contrast of DHFLC cells can be improved, but provide no directions as to how to achieve contrast greater than 40:1. They employed shear alignment techniques to obtain the DHFLC cell with 40:1 contrast ratio. Shear alignment techniques are not, however, practical for large scale manufacture. More practical alignment techniques involving uni-directional rubbing or brushing of alignment layers have been reported to give contrast ratios in DHFLC cells of only 12:1. EP 309,774 refers to a DHF cell having a contrast ratio of 100:1, but provides no detail as to how this contrast was achieved.

The inventors have discovered that methods analogous to those that had been successful in improving the alignment and contrast of SSFLC cells can be employed to improve the alignment and contrast in DHFLC cells. The inventors have discovered that N* pitch sufficiently long to facilitate alignment and more specifically planar alignment and "bookshelf" alignment of a DHFLC cell can be achieved in FLC compositions that also possess the tight ferroelectric phase pitch required for DHFLC cells which are stable to helix unwinding. FLC compositions having a tight pitch ferroelectric phase, e.g., a smectic C* phase, and a long pitch N* phase at higher temperatures can be aligned using methods such as those described in WO 87/06021. These methods combine cell surface treatment (i.e., alignment layers) with cooling of the FLC in contact with the treated surfaces of the cell plates from the nematic phase to the ferroelectric phase. Good FLC alignment and high DHFLC cell contrast result. DHFLC cells with high contrast, i.e., 40:1 or higher, and preferably 100:1 or higher, can be made by these methods. Cooling of the FLC from the nematic phase to the ferroelectric phase may be accompanied by application of an electric field across the FLC layer. It has also been found that the presence of an orthogonal smectic phase, such as a smectic A phase, intermediate in temperature between the nematic and the ferroelectric phases further facilitates good alignment and the generation of high contrast cells.

More specifically, the inventors have discovered chiral nonracemic dopants which, in combination with appropriate hosts, induce tight ferroelectric phase pitch without inducing tight pitch in chiral nematic phases. It has been found that both the FLC host and chiral nonracemic tight, pitch dopant influence the relative magnitudes of the ferroelectric, e.g., smectic C*, and the N* phase pitch.

As is conventional, a ferroelectric liquid crystal cell of the present invention comprises an FLC layer of known thickness (d) between retaining plates. As shown for example in the DHFLC cell 10 of FIG. 1, a cell has plates 11 and 12 and FLC layer 15. The plates can be made of glass, plastic or other materials having suitable optical properties and are essentially parallel to each other. At least one of the plates is transparent or semi-transparent. In a transmission-mode device, both plates are typically transparent or semitransparent. In a reflection-mode device, one of the plates has a reflective surface, such as a metal sheet or a deposited reflective surface. The plates are provided with electrodes such that a voltage can be applied to the electrodes to generate an electric field across the FLC layer. For example, transparent or semi-transparent conducting layers (13, 14) can be provided on the inner surface of the plates, again as shown in FIGS. 1. Suitable transparent or semi-transparent electrode materials include among others tin oxide and indium tin oxide. In a reflective-mode device employing a metal mirror, the reflective surface may also serve as an electrode.

Electrode may be a single contiguous sheet, provided, for example, as a layer deposited over an entire plate or may be deposited or laid down in a desired pattern, provided, for example, as a grid over the plate to form pixels. Spacers may be employed between the plates to obtain the desired FLC thickness.

FLC cells of the present invention can be provided with alignment layers on the inside surfaces of the electrode plates in contact with the FLC layer to induce a desired FLC alignment or assist or improve the FLC alignment within the cell. To obtain good alignment and high contrast, the use of alignment layers are preferred. For example, a nylon, polyamide, polyimide or other polymeric layer can be provided on the inner surfaces of the plates. Such alignment layers are rubbed or brushed in one direction (unidirectional rubbing), for example with a soft rayon cloth. The layers on opposite plates are rubbed in the same direction, but rubbing can be parallel or antiparallel on opposite plates. Providing a rubbed or bushed alignment layer on the cell plates is also termed cell surface treatment. These surface treatments effect, assist or improve alignment of the FLC molecules in the FLC layer as is appreciated in the art. Other alignment techniques for FLCs include shearing procedures and oblique vaporization of $SiO_x$ onto the inner surfaces of the cell plates. Alignment techniques can be used to achieve a desired alignment, for example, either planar or homeotropic alignment, appropriate to a particular application.

DHFLC cells are FLC cells which retain helical director structure within the FLC layer and are, thus, not surface-stabilized. The helical director structure of a DHF cell is illustrated in FIG. 1. Within a smectic layer, the average molecular long axis ñ is oriented at an angle ($\psi$) to the layer normal ẑ. Ferroelectric materials possess spontaneous polarization P which is parallel to the layer planes and perpendicular to n̂. In aligned FLCS, n̂ and P spiral around ẑ from smectic layer to smectic layer as indicated in FIG. 1. P and n̂ of successive layers spiral through an azimuthal angle, ø, forming the helical director structure illustrated in FIG. 1. The layer normal is parallel to the helical axis. The distance along the helical axis between n̂ and P having the same orientations, i.e., for a change in ø of 360°, is the magnitude of the helical pitch. Pitch can be + or − indicating opposite signs of helical twist. The helical structure of the DHFLC layer may be present substantially throughout the FLC layer or only present in the central portion of the FLC layer. Sufficient helical structure must be present in the layer so that a given cell exhibits a DHF-effect. It may be, for example, that the helical director structure of the FLC is disrupted in the vicinity of the plate surfaces due to surface interactions. Preferred DHFLC cells are those in which the presence of the helical structure of the FLC layer is maximized. DHFLC cell contrast is improved by good FLC molecular alignment. Alignment techniques for DHF cells should be such that alignment is facilitated without complete disruption of helical structure. Preferred alignment techniques for DHF cells are those which allow good alignment without substantial disruption of helical director structure. The inventors have found that the use of parallel-rubbed nylon alignment layers is preferred for production of high contrast DHF-effect cells. As discussed above, the DHF-effect is now well-known in the art. A DHFLC cell or DHFLC device containing such a cell is one in which the application of incremental voltage change to the cell electrodes results in an incremental distortion of the helical structure of the FLC layer and, as a consequence of this distortion, there is an incremental change in the detected optical anisotropy of the cell. As is also understood in the art, a DHFLC cell exhibits an incremental change in orientation of its optic axis as well as an incremental change in birefringence with an incremental voltage change. Both of these effects contribute to the detected change in optical anisotropy as a function of voltage.

FLCs that are half-wave plates have particular advantages for use in electro-optical devices. Half-wave plates are designed such that:

$$\Delta nd = \lambda/2$$

Half-wave plate FLC cells require lower operating voltages and are more useful for broad band applications than higher order, cells (e.g., 3/2λ etc.).

The variation of transmission of a half-wave FLC cell with wavelength is considerably less than with higher order cells. This is particularly true for applications in the visible where an FLC half-wave plate designed such that $\Delta nd = \lambda/2$ at about $\lambda=550$ nm is essentially an achromatic half-wave plate over the entire visible spectrum.

The very tight ferroelectric pitch mixtures of this invention enable the construction of DHF cells stable to unwinding which can be designed to be half-wave ($\Delta nd = \lambda/2$). High contrast FLC cells in which $d(\lambda/2\Delta n)$ is between about 0.25/$\Delta n$ μm and 0.30/$\Delta n$ μm are included in this invention.

N* and ferroelectric pitch can be measured by any method known to the art. The Cano wedge method can be employed to measure either ferroelectric (i.e., smectic C*) or N* pitch in samples having a pitch longer than about 0.5 to 0.6 μm. See: R. Cano (1967) Bull. Soc. France Mineral Crystallogr. XC 333; P. Kassubek and G. Meier (1969) Mol. Cryst. Liq. Cryst. 8:305–315; Ph. Marinot-Lagarde et al. (1981) Mol. Cryst. Liq. Cryst. 75:249–286. Selective reflectance measurements of thick (about 400 μm) homeotropically aligned cells are typically employed to measure pitch of magnitude less than about 0.5 μm. See: K. Kondo et al. (1982) Jpn. J. Appl. Phys. 21:224.

The ferroelectric and N* pitch of a FLC material vary as a function of temperature. Typically, ferroelectric pitch tends to decrease with decreasing temperature and N* pitch tends toward infinity at the transition point between the N* phase and the lower temperature smectic phase. Often N* pitch decreases very rapidly within a few tenths of a degree above the N* transition point. Nematic phase pitch compensation agents can be employed to lengthen N* pitch at temperatures above the transition point. The compositions of the present invention combine long N* pitch at least about 1°–2° C. above the transition point with tight ferroelectric pitch at useful device operating temperatures (about 10°–80° C.).

Figure 4:
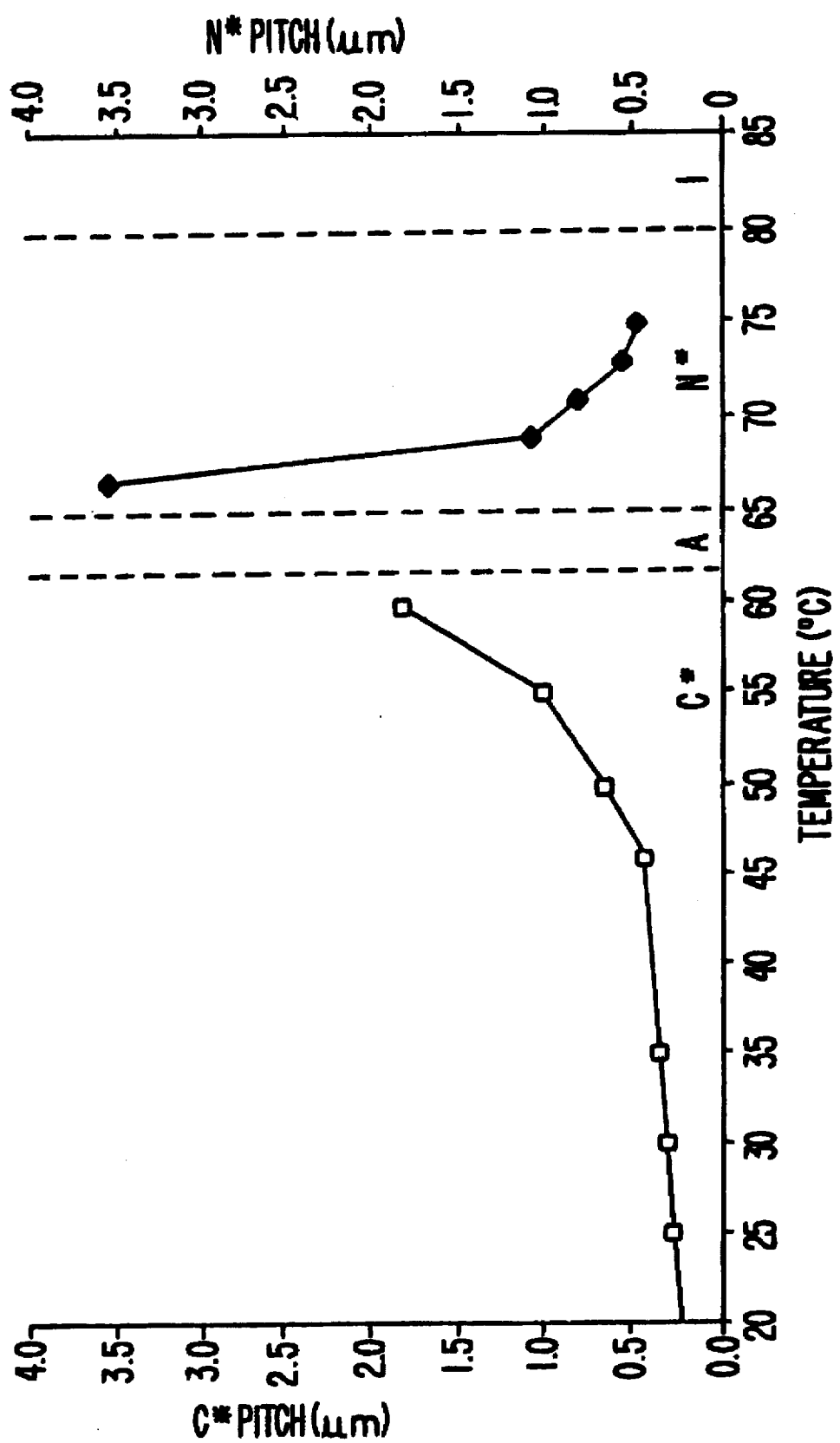
FIG. 4 shows a graph of pitch magnitude vs. temperature for a representative FLC mixture of this invention, Mixture 1.

FIG. 4 shows how the magnitude of C* and N* pitch of a representative mixture of this invention vary as a function of temperature. N* pitch is plotted on a scale ten-fold higher than C* pitch in FIG. 4. The C* pitch and the N* pitch of Mixture 1 are always negative (i.e., a − sign of pitch or twist). This mixture has an orthogonal smectic phase, here a smectic A phase, intermediate between the chiral smectic phase (smectic C*) and the chiral nematic phase. Starting from above the A to N* transition, as temperature is decreased the magnitude of the N* pitch increases toward infinity. In this mixture, the N* pitch is about 5 μm about 10° C. above the A-N* transition, about 7.5 μm at about 5° C. above that transition and at about 2° C. above that transition increases to over about 35 μm. As the temperature approaches the A-N* transition point, N* pitch increases toward infinity.

FLC mixtures of the present invention exhibit long N* pitch at 1°–2° C. above the transition point into the N* phase and preferably exhibit long N* pitch at least up to 5° C. above that transition point and most preferably have long N* pitch over the entire N* phase. N* pitch measurement can be readily made at temperatures of about 1°–2°C. above the N* transition point or higher. As the temperature approaches to within about 1° C. of the transition point, it becomes difficult to obtain accurate N* pitch measurements.

Also as indicated in FIG. 4, C* pitch can vary as a function of temperature. Mixture 1 has C* pitch less than about 0.5 μm at room temperatures (20°–30° C.). FLC mixtures of this invention preferably have tight pitch at temperatures useful for the operation of optical devices. The useful operating temperatures will vary dependent upon the type of device and its application. In some applications, tight C* pitch at room temperatures will be desirable. In other applications, it may be necessary or desirable to operate at higher temperatures. In such cases, FLCs having tight C* pitch at temperatures above room temperature, e.g., 40°–80° C., will be desirable.

High contrast DHF cells of the present invention are produced by introducing an FLC mixture of this invention between spaced electrode plates. The inside surface of the electrode plates is preferably provided with a surface treatment that facilitates alignment, such as a uni-directionally-rubbed polymer layer. The treated plates are oriented with respect to each other such that the rubbing directions of the alignment layers on opposite plates are parallel or antiparallel. The FLC mixture is introduced between the cells at a temperature at least 5° C. above the N* transition point. Preferably the FLC mixture is introduced between the plates at a temperature such that it is in the isotropic phase. The FLC is then cooled into the N* phase and cooled slowly from at least about 5° C. above the N* transition point into the ferroelectric phase. The FLC is cooled at a rate of about 0.050 to 2° C./minute from within about 5° C. of the N* transition point to the lower smectic phase. If an orthogonal smectic phase is present, the FLC is slowly cooled through the orthogonal smectic phase into the lower temperature ferroelectric phase.

The resulting aligned DHFLC cell is then examined to assess alignment as is known in the art, for example, by measuring the contrast ratio of the cell. If desired, one or more additional steps of heating to the N* phase followed by slow cooling to the ferroelectric phase can be employed to obtain improved alignment. It is preferred that the alignment procedure be repeated until substantial alignment is achieved. Substantial alignment of a DHF cell is such that less than about 0.025% of incident light leaks through the cell when it is positioned for minimal transmission (OFF STATE) between crossed polarizers. Preferred alignment is that which allows less than about 0.01% leakage of incident light in the OFF STATE. DHF cells having high contrast result from this cell alignment procedure.

FLC compositions which have phase and pitch properties useful in the devices of the present invention are exemplified by compositions which contain tight ferroelectric phase pitch dopant with chiral nonracemic 2,3-dihaloalkoxy tail groups, such as those described in U.S. Pat. No. 5,051,506 and U.S. patent applications Ser. Nos. 07/763,134 and 07/556,656. Compounds of formula I:

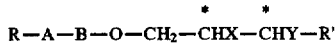

R—A—B—O—CH$_2$—CHX—CHY—R'  I where A, B, X, Y and R are as defined above and R' is an alkyl, alkenyl, alkylsilyl or other group as defined above, can be synthesized by methods described in U.S. Ser. No. 07/763,134 or by routine modification of those methods. Compounds of formula I where R' is an acyl group can be synthesized by methods described in U.S. Ser. No. 07/556,656 or by routine modification of those methods. The methods noted above can be readily adapted by known expedients, such as described in PCT applications WO 89/10356, WO 87/05015 or WO 86/06401 or U.S. Pat. No. 4,886,622, for the synthesis of compounds of formula I which contain trans-1,4-cyclohexylene groups.

FLC compositions which have phase and pitch properties useful in the devices of the present invention are exemplified by compositions which contain tight ferroelectric phase pitch dopants and a host which comprises at least about 10% by weight of one or more of the dialkoxy compounds of formula II:

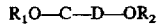

R$_1$O—C—D—OR$_2$  II where R$_1$, C, D and R$_2$ are as defined above.

Compounds of formula II suitable as host components are either commercially available or can be synthesized by well-known methods or by the routine adaptaion of well-known methods, such as those provided in EPO application EP 307,880 and Swiss application CH 593,495.

Hosts of the present invention can contain, in addition to the compounds of formula II, one or more of the compounds of formulas III and IV:

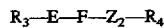

R$_3$—E—F—Z$_2$—R$_4$  III or

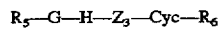

R$_5$—G—H—Z$_3$—Cyc—R$_6$  IV where R$_3$, R$_4$, R$_5$, R$_6$, E, F, Z$_2$, G, H, Z$_3$ and Cyc are as defined above.

Compounds of formula III or IV, suitable in the hosts of this invention, are either commercially available or can be prepared by methods well-known in the art or by routine adaptation of well-known methods.

A chiral nonracemic dopant which has tight C* pitch-induction properties useful in the devices of this invention can be selected by routine testing by the following procedure:

Mixtures of 10–50% by weight of the chiral nonracemic molecule to be tested (i.e., the candidate dopant) with a room temperature smectic C or C* host compound comprising at least about 10% by weight of a dialkoxy compound of formula II, preferably the smectic C hosts Hi, H2 (the compositions of which are provided in the Examples) are prepared. Mixtures of acceptable dopants will exhibit a smectic C* phase and a chiral nematic phase at higher temperatures at some dopant concentration between about 10% and 50% by weight. Candidate chiral nonracemic molecules which destroy the smectic C or nematic phase in all such mixtures are not acceptable tightpitch dopants of this invention. The C* and N* pitch of the mixtures with the candidate dopants are measured. N* pitch is measured at temperatures about 1°–2° C. above the transition point into the N* phase. C* pitch is measured in the useful device operating temperature range (about 10°–80° C.). Most typically, N* pitch is measured at about 2° C. above the N* transition point and C* pitch is measured at room temperature (20°–30° C.). Acceptable tight pitch dopants are those in which in at least one of the mixtures the N* pitch/C* pitch ratio is about one or more. Preferred tight-pitch dopants are those in which in at least one mixture the N* pitch/C* pitch ratio is about 4 or more. With more preferred dopants, at least one of the test mixtures will exhibit N*/C* pitch ratio of about 10 or more. Preferred dopants are those in which at least one of the test mixtures exhibits smectic C* pitch less than about 0.25 µm at room temperatures and N* pitch up to about 2° C. above the transition point of about 2.5 µm or more. More preferred dopants are those in which at least one of the mixtures have C* pitch of about 0.15 or less at room temperature. Preferred dopants are those which induce tightest C* pitch without decreasing the N* pitch below about 4 µm at dopant concentrations below about 10–20% (w/w). This procedure can be readily adapted to select chiral dopants which induce tight ferroelectric pitch in any chiral tilted smectic phase.

A smectic C or C* host that is suitable for use in combination with tight pitch-inducing dopants of the present invention can be selected by routine testing by the following procedure:

Candidate smectic C or C* hosts exhibit a smectic C or C* phase and preferably a nematic phase at higher temperatures. Hosts preferred for device applications have a smectic C or C* phase at useful device operating temperatures (10°–50° C.). Preferred candidate hosts have an orthogonal smectic phase, for example, a smectic A phase, intermediate in temperature between the smectic C or C* and nematic phases. Mixtures of a candidate host with 10–50% of one of the specifically exemplified tight pitch dopants of this invention: MDW128, MDW232, MDW116, MDW198, MDW316, or MDW317, as defined in the Examples, are prepared. Hosts suitable for testing by this procedure must mix with at least one of the exemplified dopants at a concentration between about 10–50% (w/w) of dopant. The C* and N* pitch of the mixtures with the candidate dopants are measured. N* pitch is measured at temperatures about 1°–2° C. above the N* transition point. C* pitch is measured at useful device operating temperatures about 10°–80° C. Most typically, C* pitch is measured at 2° C. above the transition point and C* pitch at room temperature. Hosts suitable for use in the compositions of this invention are those in which the N* pitch/C* pitch ratio of at least one of the tested mixtures is about one or more. Preferred hosts are those in which the N* pitch/C* pitch ratio of at least one of the mixtures is about 4 or more. In more preferred hosts, the N*/C* pitch ratio will be about 10 or more. Preferred hosts are those in which at least one of the mixtures exhibits smectic C* pitch less than about 0.25 μm at room temperature and N* pitch up to about 2° C. above the N phase transition point of about 2.5 μm or more. More preferred hosts at those in which at least one of the mixtures have C* pitch of 0.15 or less at room temperature.

This procedure can be readily adapted to select any ferroelectric hosts. Once a tight pitch-inducing chiral dopant is identified by the procedure described herein above, that newly-identified dopant can be employed in the assay for ferroelectric phase hosts in place of the dopant compounds specifically identified above. Due to mixing incompatibilities or other factors, a particular dopant of this invention may not induce tight pitch in all ferroelectric phase, smectic C or smectic C* hosts of this invention.

Hosts are typically achiral or are chiral, nonracemic materials having low polarization density.

The following examples are intended to illustrate the practice of this invention and are in no way intended to limit its scope.

EXAMPLES

In the following Examples, chiral FLC dopants of formula:

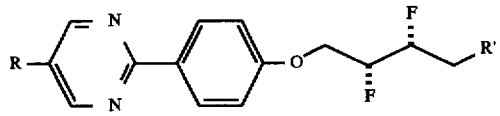

where R and R' are as listed and were introduced into FLC host mixtures and the C* and N* pitch of the resulting mixtures were determined.

TABLE 1

Exemplary FLC dopants

| R | R' | Designation | nC/cm² | Sign of Helical Twist C*/N* |
|---|---|---|---|---|
| C₆H₁₃ | C₃H₇ | MDW128 | 187¹ | −/− |
| C₈H₁₇ | C₃H₇ | MDW232 | 270¹ | −/− |
| C₉H₁₉ | C₃H₇ | MDW116 | 250¹ | −/− |
| C₁₀H₂₁ | C₃H₇ | MDW198 | 247¹ | −/− |
| C₆H₁₃ | —OCOCH₃ | MDW316 | 350² | −/− |
| C₆H₁₃ | —OCO₂H₅ | MDW317 | 396² | −/− |

¹) Extrapolated from measurements of Ps at 25° C. in H1 host.
²) Extrapolated from measurements of Ps in chiral or racemic 4'-methylhexlyoxyphenyl-4-n-decyloxybenzoate.

Pitch measurements were performed using standard methods: the Cano wedge technique or by selective reflectance as described, for example, in R. Cano (1967) supra and K. Kondo et al. (1982) supra. For all phase diagrams, temperatures are given in °C and I=isotropic, N*=chiral nematic, A=smectic A, C*=chiral smectic C, C=smectic C, and X=crystalline.

Example 1
Dependence of C* and N* Pitch on Type of Host.

Mixtures of MDW116 with three types of FLC host were assessed for C* and N* pitch as described above. The results of the assessment of mixtures containing 10% by weight of these hosts is shown in Table 1.

TABLE 2

N* and C* Pitch of 10% Mixtures of MDW116 with Various Types of Smectic C* Hosts

| Type of Host | N* Pitch | C* Pitch |
|---|---|---|
| dialkoxyphenyl-pyrimidine | −4.5 | −1.0 |
| alkylalkoxy-phenylpyrimidine | −5.3 | −3.0 |
| phenylbenzoate | −0.8 | −2.7 |

The host plays a dramatic role in pitch induction by the dopant in the mixture. C* pitch can be varied as much as 3-fold and the N* pitch by over 5-fold by changing the host.

Dialkoxy hosts provided the tightest C* pitch while maintaining a long N* pitch.

Example 2
Tight C* Pitch FLC Mixtures.

Difluoroalkoxy dopants induce tight pitch in dialkoxyphenylpyrimidine hosts. Table 3 summarizes C* and N* pitch measurements of mixtures of 30% by weight of selected dopants in a selected dialkoxyphenylpyrimidine host H1.

TABLE 3

C* and N* Pitch Measurements

| Dopant | C* Pitch¹ (HTP)³ | N* Pitch² (HTP)³ | Phase Diagram of Mixture |
|---|---|---|---|
| MDW128 | −0.36 μm (−9.3) | −1.5 μm (−2.2) | I--79--N*--66--A--56--C* |
| MDW116 | −0.24 μm (−13.9) | −1.4 μm (−2.4) | I--80--N*--65--A--61--C* |
| MDW232 | −0.22 μm (−15.2) | −1.3 μm (−2.6) | I--79--N*--57--C* |
| MDW198 | <−0.15 μm (>−22.2) | −1.0 μm (−3.3) | I--80--N*--50--C* |

¹Measured at 20° C.
²Measured at 2° C. above N* phase transition.
³HTP = Helical Twisting Power = $\left( \text{pitch} \times \frac{\text{w/w \%}}{100} \right)^{-1}$ H1 is an achiral smectic C host material having the composition (in weight %):

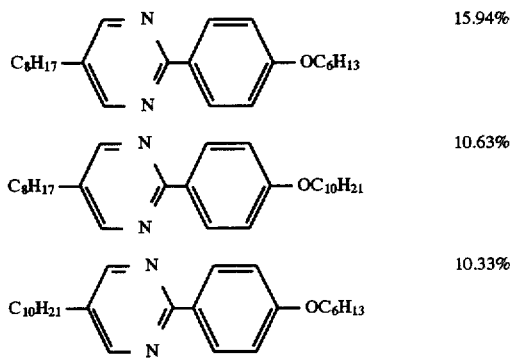

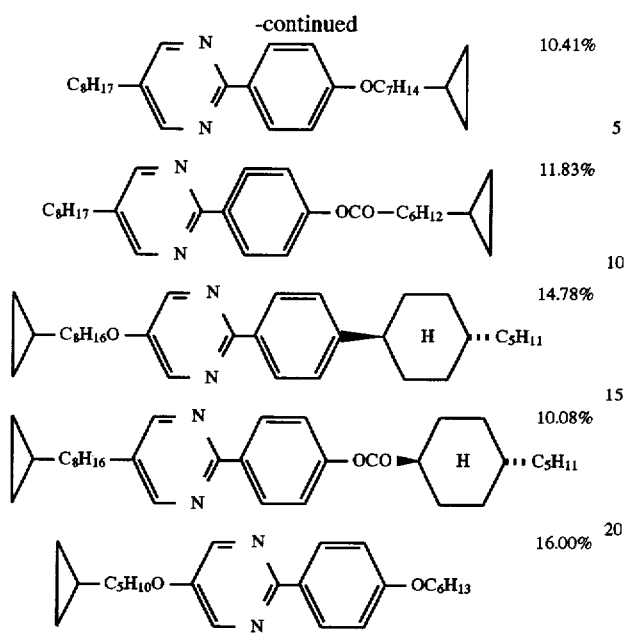

H1 has the following phase diagram: I—89—N—70—A—66—C

Example 3
Variation in C* and N* Pitch as a Function of Dopant Concentration.

Mixtures of MDW232 in a smectic C* host, H2, which comprises dialkoxyphenylpyrimidines, were prepared and the C* and N* pitch of the mixtures were measured. As shown in Table 4, as the weight % of the dopant in the mixture is increased, the C* pitch gets tighter. The ratio of N*/C* pitch in these mixtures is at least 8 and in the 30% mixture the ratio is greater than 10.

and its phase diagram is I—93—N—78—A—71—C.

Example 4
N* Pitch Compensated Mixtures.

TABLE 4

C* and N* Pitch Measurements

| MDW232 Wt. % | C*[1] Pitch (HTP)[3] | N*[2] (HTP)[3] | Pitch/ Ratio N*/C* | Phase Diagram of Mixture |
|---|---|---|---|---|
| 10% | −0.57 μm (−17.5) | −4.8 μm (−2.1) | 8.4 | I—92—N*—75—A—71—C* |
| 20% | −0.30 μm (−16.7) | −2.4 μm (−2.1) | 8.0 | I—87—N*—69—A—66—C* |
| 30% | <−0.15 μm (>−22.2) | −1.6 μm (−2.1) | <10.7 | I—84—N*—63—C* |

[1]Measured at 20° C.
[2]Measured at 2° C. above N* phase transition.
[3]HTP = Helical Twisting Power = $\left( pitch \times \frac{w/w\ \%}{100} \right)^{-1}$ H2 is an achiral smectic C host of composition (in weight k%):

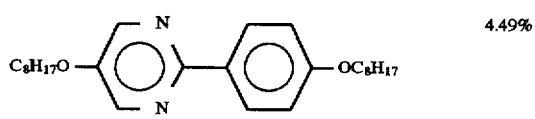

4.49%

All of the following mixtures have a C* pitch less than 1 μm and an N* pitch greater than 10 μm.

Mixture 1 has the composition:
10% MDW198
15% MDW116
0.8% ZLI4572
74.2% FELIX008

ZLI4572 is a commercially available pitch compensating agent having the phase diagram: I—133—X:

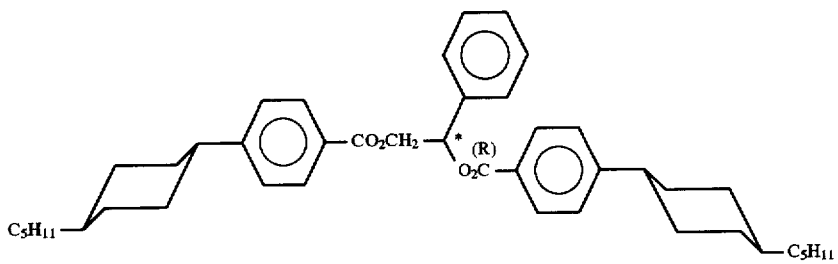

Mixture 1: C* pitch (25° C.)=–0.27; N* pitch (2° C. above N* phase transition)=–38 μm and phase diagram is:

I—80—N*—65—A—62—C—<25—X

Figure 2:
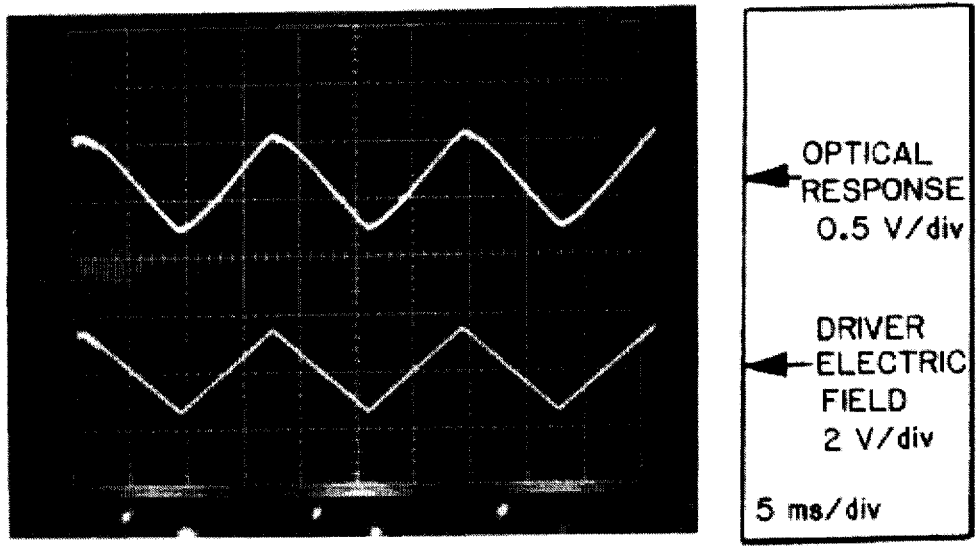
FIG. 2 is a graph showing linear optical response of a planar aligned DHFLC cell of the present invention on application of a linear driving voltage. The DHFLC cell is 2.5 µm thick and contains DHFLC Mixture 1 of Example 4.
Figure 3A:
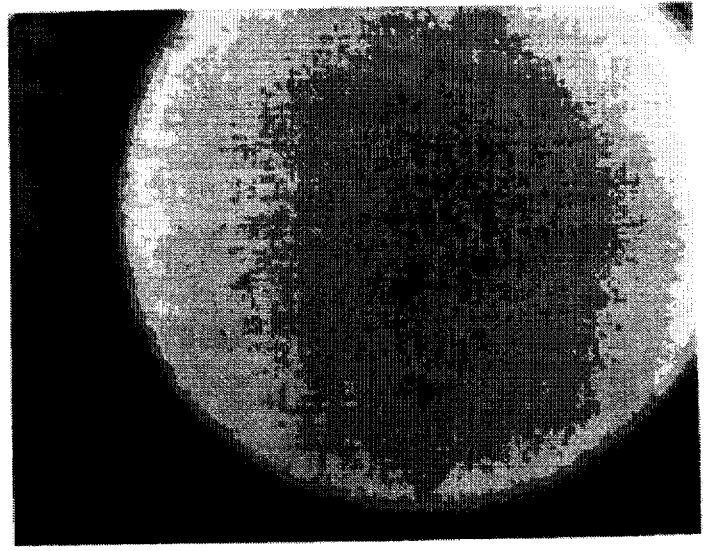
FIG. 3 is a comparison of alignment of a DHFLC cell of the present invention (2.5 µm cell with Mixture 1), view A, with a 2.5 µm DHFLC cell using a commercially available DHF mixture 5679 (Hoffman La Roche), view B. Views A and B are photomicrographs of the texture of the cells. The DHFLC cell containing Mixture 1 of this invention is much smoother in texture than of the prior art DHFLC mixture indicative of superior alignment of the cell of view A. The DHFLC cell containing Mixture 1 has a contrast ratio of 158:1, while that containing 5679 has a contrast ratio of 25:1.
Figure 3B:
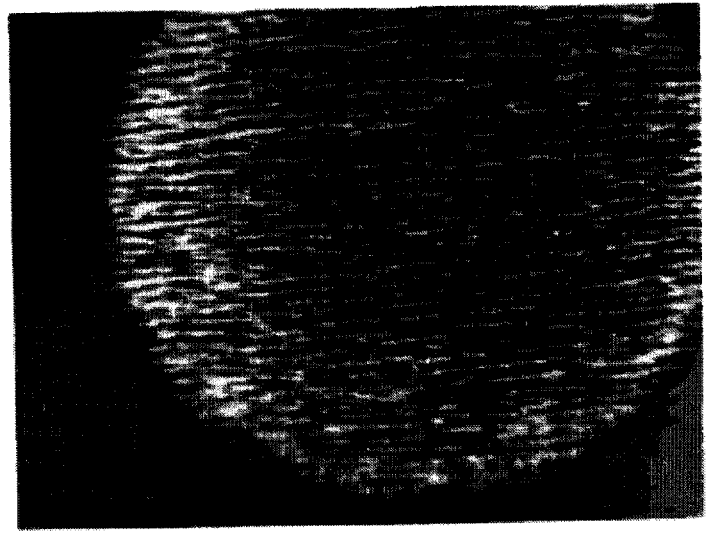

FIG. 2 illustrates the DHF-effect in a 2.5 μm thick DHF cell containing a bookshelf aligned layer of Mixture 1. Optical response in the cell is approximately linear with applied driving electric field.

Mixture 2 has the composition:
10% MDW316
10% MDW317
0.7% ZLI4572
79.3% FELIX008

Mixture 2: C* pitch (22° C.)=–0.21 μm; N* pitch=–30 μm and phase diagram is:

I—72—N—58—A—45—C*—<22—X

Mixture 3 has the composition:
10% MDW198
20% MDW232
0.9% ZLI4572
69.1% H2

Mixture 3: C* pitch (22° C.)=–0.19 μm, N* pitch=–36 μm and phase diagram is:

I—82—N*—55—C*—<22—X

FELIX008 is a commercially available FLC mixture having the phase diagram:

I—86—N*—75—A—70—C*—(–7)—X and FELIX008 has a polarization of –9.6 nC/cm².

Example 5
Comparison of Contrast of DHF Cells.

Two DHF cells (2.5 μm thick) were prepared employing a commercial DHF mixture (Hoffman La Roche 5679) and Mixture 1 (above).

Transmission-mode 2.5 μm cells were prepared by coating the inside surfaces of the plates with ITO (Indium tin oxide) electrode layers. A nylon layer was spun onto the electrode plates and dried. The nylon layer was rubbed in one direction using a soft rayon cloth. The alignment layers were rubbed in a parallel direction on opposite plates. The plates were spaced and assembled such that the rubbing directions were parallel and in the same direction. The FLC mixture was heated to 100° C. and introduced into the cell by capillary action. The FLC mixture was slowly cooled within the cell at a rate of about 0.5° C./minute until the smectic C* phase was reached. This treatment results in planar aligned cells. Both cells, one containing Mixture 1 and one containing Roche 5679, were positioned between crossed polarizers and an appropriate voltage applied to the electrodes to vary the optical anistropy of the cells. The texture of the cells and the contrast of the cells were examined under the same conditions.

Photomicrographs of the texture of the two cells are shown in FIG. 2. View A, Mixture 1 and View B. The texture of the Mixture 1 cell is much smoother. The contrast of the Mixture 1 cell was significantly higher (158:1) than that of the 5679 containing cell (25:1).

Those of ordinary skill in the art to which this invention pertains will appreciate that the methods, techniques procedures, compounds and compositions specifically described herein can be altered, modified or substituted with functional equivalents to achieve the goals of this invention without departing from the spirit and scope of this invention. All such alterations, modifications substitutions and functional equivalents are intended to be encompassed by this invention.

We claim:

1. A ferroelectric liquid crystal composition comprising a chiral dopant and a host mixture which exhibits a ferroelectric phase and a chiral nematic phase at temperatures above said ferroelectric phase, wherein the natural helix pitch in said nematic phase at temperatures at least about 1°—2° C. above the N* transition point is at least about 4 times longer than the natural helix pitch in said ferroelectric phase at about room temperature, wherein said chiral dopant is a chiral nonracemic compound of the formula:

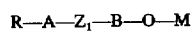

R—A—Z₁—B—O—M wherein A and B are, independently of one another, selected from 1,4-phenylene, 1,4-phenylene in which one or two of the ring carbon atoms are replaced with nitrogen atoms, a 1,4-cyclohexylene. $Z_1$ is a single bond, a —CO—O— group, a —O—CO—group, or an O atom if one of A or B is a 1,4-cyclohexylene. R is a group having from one to twenty carbon atoms in which one or more non-neighboring carbon atoms can be replaced with a double bond, an O atom, a S atom or a Si(CH₃)₂ group, and O-M is a 2,3-dihaloalkoxy moiety of the formula:

—O—CH₂—CHX—CHY—CH₂—R' where * represents an asymmetric carbon, X and Y, independently of one another, are halogens, R' is a group having from one to about twenty carbon atoms in which one or more non-neighboring carbon atoms can be replaced with a double bond, an O atom, a S atom or a Si(CH₃)₂ group, or is an acyl group —OCO—R" where R" is a group having from one to twenty carbon atoms and wherein one or more non-neighboring carbon atoms can be replaced with a double bond, an O atom, a S atom or a Si(CH₃)₂ group.

2. The ferroelectric liquid crystal composition of claim 1 wherein said dopant is a chiral nonracemic 2,3-difluoroalkyloxy compound of the formula:

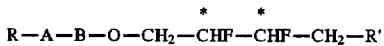

where * represents an asymmetric carbon, one of A or B is a 1,4-phenylene and the other of A or B is a 2,5-phenylpyrimidine and wherein R' is an alkyl group having from one to twenty carbon atoms or an acyl group —OCO—R" where R" is a group having from one to twenty carbon atoms.

3. The ferroelectric liquid crystal composition of claim 2 wherein the configuration of said dopant is 2-R,3-R or 2-S, 3-S.

4. The ferroelectric liquid crystal composition of claim 2 wherein R' is an alkyl group having from one to twenty carbon atoms.

5. The ferroelectric liquid crystal composition of claim 2 wherein R' is an acyl group having from one to twenty carbon atoms.

6. The ferroelectric liquid crystal composition of claim 1 which comprises a host material which comprises at least about 10% by weight of one or more compounds of the formula:

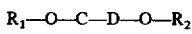

in which one of C or D is a 1,4-phenylene and the other of C or D is a 1,4 phenylene in which one or more of the carbon atoms of the ring are replaced with a nitrogen atom and wherein $R_1$ and $R_2$ are, independently of one another, alkyl or alkenyl having from one to twenty carbon atoms or alkylsilyl groups having from four to twenty-two carbon atoms.

7. The ferroelectric liquid crystal composition of claim 6 herein $R_1$ and $R_2$ are, independently of one another, alkyl or alkenyl groups having from one to twenty carbon atoms.

8. The compound of claim 1 further comprising a nematic phase pitch compensation agent.

9. The ferroelectric liquid crystal composition of claim 1 further comprising one or more compounds of the formula:

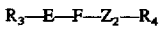

where $R_3$ and $R_4$ are, independently of one another, alkyl or alkenyl groups having from one to about twenty carbon atoms or an alkylsilyl group having from about four to about twenty-two carbon atoms and where one of E or F is a 1,4-phenylene and the other of E or F is a 1,4-phenylene in which one or two of the ring carbons are replaced with a nitrogen atom and $Z_2$ is an oxygen atom, a —CO—O— or a —O—CO—group.

10. The ferroelectric liquid crystal composition of claim 9 wherein $Z_2$ is an oxygen atom or a —CO—O— group.

11. The ferroelectric liquid crystal composition of claim 9 wherein $Z_2$ is an oxygen atom.

12. The ferroelectric liquid crystal composition of claim 9 wherein one of E or F is a 1,4-phenylene and the other of E or F is a 2,4-pyrimidine.

13. The ferroelectric liquid crystal composition of claim 9 wherein $R_3$ and $R_4$ are, independent of one another, an alkyl or alkenyl group having from one to twenty carbon atoms.

14. The ferroelectric liquid crystal composition of claim 1 further comprising one or more compounds of the formula:

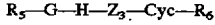

where $R_5$ and $R_6$ are, independently of one another, alkyl or alkenyl groups having from one to twenty carbon atoms or an alkylsilyl group having from about four to about twenty- two carbon atoms, where one of G or H is a 1,4-phenylene and the other of G or H is a 1,4-phenylene in which one or two of the ring carbons are replaced with a nitrogen atom, $Z_3$ is a single bond, an oxygen atom, a —O—CO— group or a —CO—O— group and Cyc is a 1,4-cyclohexyl group.

15. The ferroelectric liquid crystal composition of claim 14 wherein $Z_3$ is a single bond or a —O—CO— group.

16. The ferroelectric liquid crystal composition of claim 15 wherein $Z_3$ is a —O—CO— group.

17. The ferroelectric liquid crystal composition of claim 14 wherein Cyc is a trans-1,4-cyclohexyl group.

18. The ferroelectric liquid crystal composition of claim 14 wherein one of G or H is a 1,4-phenylene and the other of G or H is a 2,5-pyrimidene.

19. The ferroelectric liquid crystal composition of claim 14 wherein $R_5$ and $R_6$ are, independently of one another, alkyl or alkenyl groups having from one to about twenty carbon atoms.

20. The ferroelectric liquid crystal composition of claim 1 wherein said chiral dopant is present in said composition at 30% or less by weight, wherein said host compound is present in said composition at 50% or more by weight and wherein said pitch compensation agent is present in said composition at a level of 1% or less by weight.

21. The ferroelectric liquid crystal composition of claim 1 which has tilt angle greater than about 18° and spontaneous polarization greater than about 10nC/cm².

22. The ferroelectric liquid crystal composition of claim 1 wherein said host compound is a smectic C or C* host.

23. The ferroelectric liquid crystal composition of claim 1 having the phase sequence: I, N*, smectic orthogonal, smectic ferroelectric with decreasing temperature.

24. The ferroelectric liquid crystal composition of claim 1 having the phase sequence: I, N*, A, C*, with decreasing temperature.

25. The ferroelectric liquid crystal composition of claim 1 wherein the natural helix pitch in said chiral nematic phase is at least about 10 times longer than the natural helix pitch in said ferroelectric phase.

26. The ferroelectric liquid crystal composition of claim 1 wherein said ferroelectric phase is a smectic C* phase.

27. The ferroelectric liquid crystal composition of claim 1 further comprising a nematic phase pitch compensation agent which exhibits the same sign of pitch in the ferroelectric phase as said chiral dopant and which exhibits the opposite sign of pitch in the nematic phase as said chiral dopant.

28. The ferroelectric liquid crystal composition of claim 1 wherein the natural helix pitch of the composition in the ferroelectric phase is 0.25 μm or less at room temperature and the natural helix pitch of the composition in the nematic phase at least about 1°-2° C. above the N* transition point is 8 μm or longer.

29. The ferroelectric liquid crystal material of claim 1 which comprises about 30% or less by weight of said chiral dopant.

30. A ferroelectric liquid crystal composition of claim 1 wherein said chiral dopant is a chiral nonracemic compound of the formula:

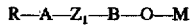

wherein A and B are, independently of one another, selected from 1,4-phenylene, 1,4-phenylene in which one or two of the ring carbon atoms are replaced with nitrogen atoms, or 1,4-cyclohexylene;

$Z_1$ is a single bond, a —CO—O— group, a —O—CO— group, or an O atom, when one of A or B is a 1,4-cyclohexylene;

R is a group having from one to twenty carbon atoms in which one or more non-neighboring carbon atoms can be replaced with a double bond, an O atom, a S atom or a Si(CH₃)₂ group;

and O-M is a 2,3-difluoroalkoxy moiety of the formula:

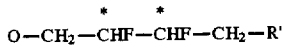
O—CH₂—CHF—CHF—CH₂—R' where * represents an asymmetric carbon, R' is a group having from one to about twenty carbon atoms in which one or more non-neighboring carbon atoms can be replaced with a double bond, an O atom, a S atom or a Si(CH₃)₂ group, or is an acyl group —OCO—R" where R" is a group having from one to twenty carbon atoms and wherein one or more non-neighboring carbon atoms can be replaced with a double bond, an O atom, a S atom or a Si(CH₃)₂ group.

31. The ferroelectric liquid crystal composition of claim 1 wherein said chiral dopant is a chiral nonracemic compound of the formula:

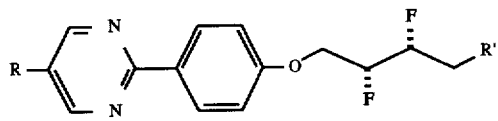

wherein R is an alkyl or alkene group having from six to twelve carbon atoms and R' is an alkyl or alkene group having from three to twelve carbon atoms or an acyl group OCOR", wherein R" is an alkyl group having from one to twelve carbon atoms, and wherein said host material is a dialkoxyphenylpyrimidine host present in said ferroelectric liquid crystal material at a level of 50% or more by weight.

32. The ferroelectric liquid crystal composition of claim 31 wherein said dialkoxyphenylpyrimidine host is a smectic C host selected from the group consisting of H1:

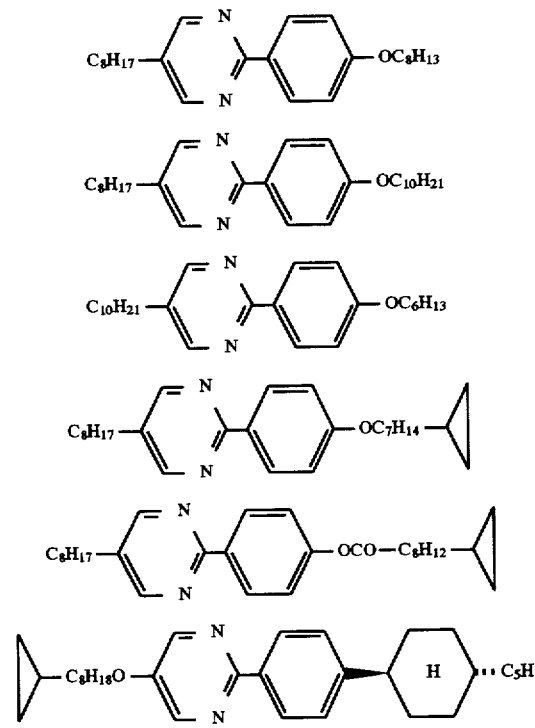

and H2:

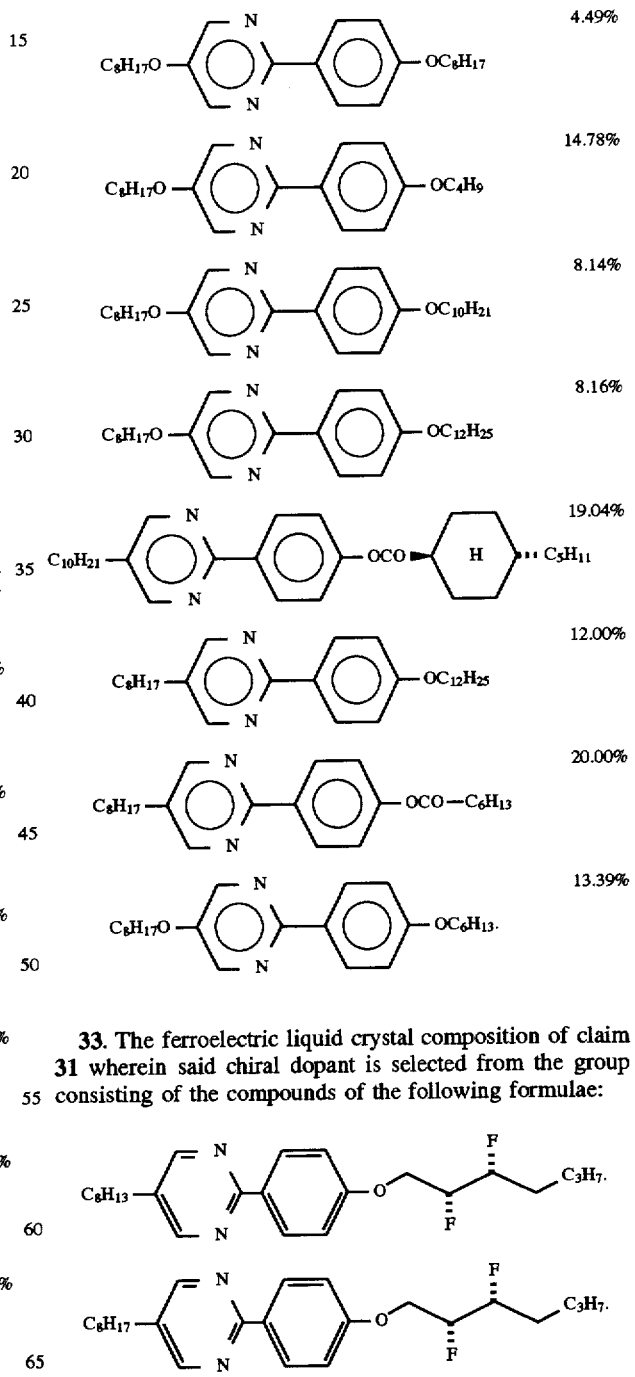

33. The ferroelectric liquid crystal composition of claim 31 wherein said chiral dopant is selected from the group consisting of the compounds of the following formulae:

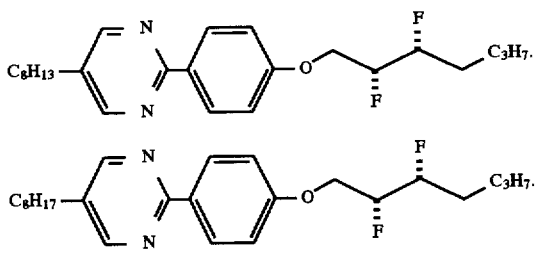

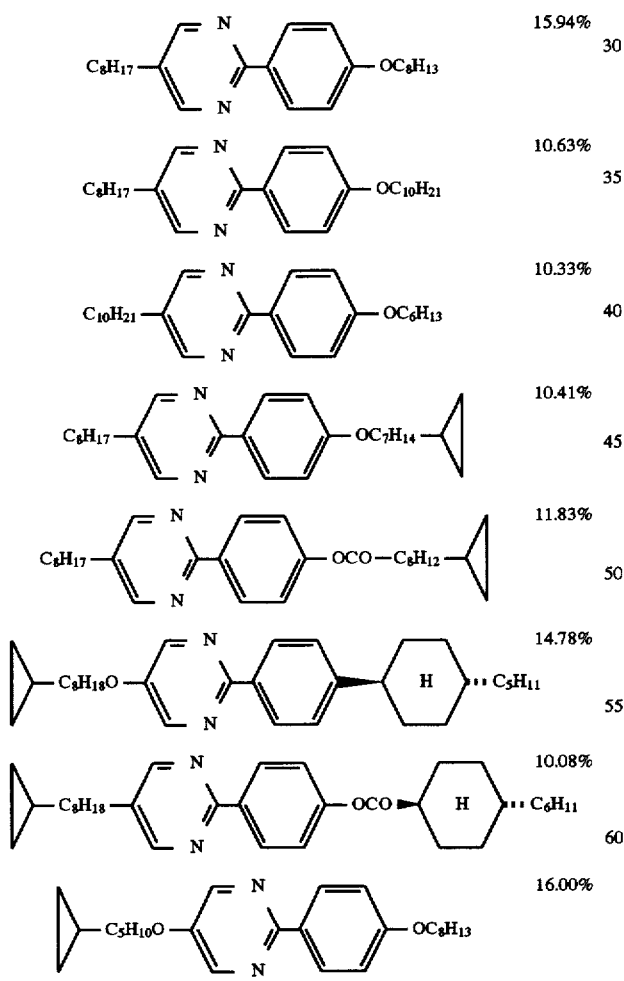

34. The ferroelectric liquid crystal composition of claim 33 wherein said dialkoxyphenylpyrimidine host is a smectic C host selected from the group consisting of H1:

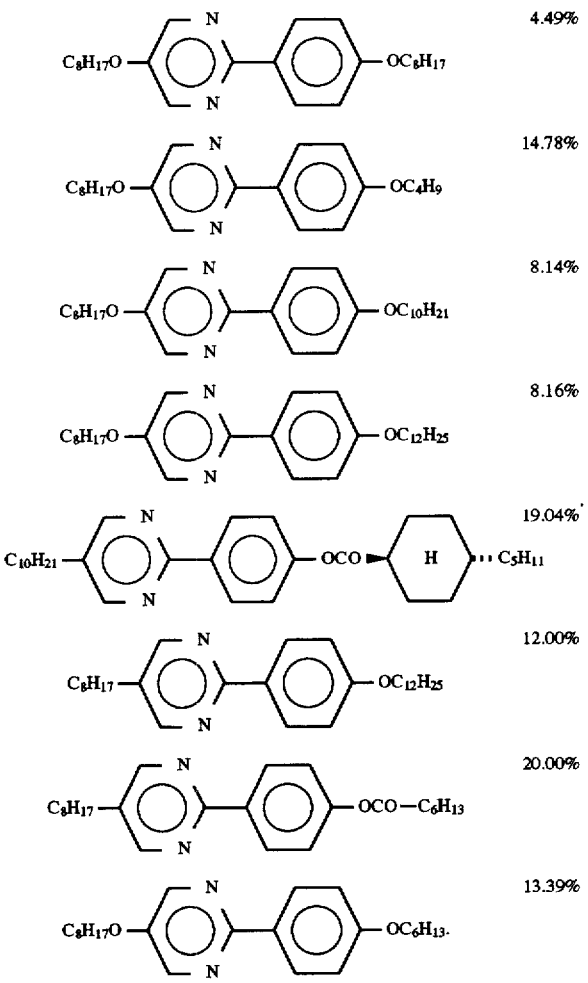

and H2:

35. The ferroelectric liquid crystal composition of claim 1 wherein the said chiral dopant is a chiral nonracemic compound of the formula:

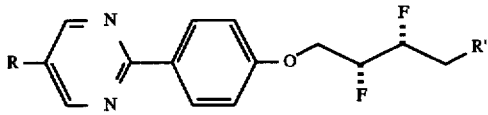

wherein R is an alkyl or alkene group having from six to twelve carbon atoms and R' is an alkyl or alkene group having from three to twelve carbon atoms or an acyl group OCOR", wherein R" is an alkyl group having from one to twelve carbon atoms, and wherein said host material is FELIX008 present in said ferroelectric liquid crystal material at a level of 50% or more by weight.

36. The ferroelectric liquid crystal composition of claim 35 further comprising a pitch compensation agent.

* * * * *

UNITED STATES PATENT AND TRADEMARK OFFICE
CERTIFICATE OF CORRECTION

PATENT NO.    :  5,753,139

DATED         :  May 19, 1998

INVENTOR(S)   :  Wand et al.

It is certified that error appears in the above-identified patent and that said Letters Patent is hereby corrected as shown below:

In column 2, line 5, remove the "," after "Unlike".
In column 2, line 17, replace '"twistk"' with --"twist"--.
In column 2, line 28, replace "orientation" with --orientations--.
In column 2, line 52, replace "+/-$E_{max}$" with --+/- $E_{max}$--.
In column 4, line 17, replace "particlarly" with --particularly--.
In column 4, line 46, replace "polymide" with --polyimide--.
In column 6, line 18, replace "dopant" with --dopants--.
In column 7, line 3, replace "acyl group-OCO-R$_A$" with --acyl group -OCO-R"--.
In column 9, in the first formula following line 51, delete the "OR" bonded to the phenyl structure and add the word "or" between the formulas.
In column 10, line 4, replace "twenty two" with --twenty-two--.
In column 10, line 16, replace "-A-$Z_1$-B-" with -- -A-$Z_1$-B- --.
In column 11, lines 61 and 65, replace "R$k_1$" with --$R_1$--.
In column 13, line 26, replace "450" with --45°--.
In column 14, line 30, replace "FIGS. 1" with --FIG. 1--.
In column 14, line 35, replace "Electrode" with --Electrodes--.
In column 15, line 9, replace "φ" with --ø--.
In column 17, line 2, replace "0.050" with --0.05°--.
In column 18, line 13, replace "Hi" with --H1--.
In column 18, line 20, replace "tightpitch" with --tight-pitch--.
In column 20, line 4, replace "Table 1" with --Table 2--.
In column 21, line 59, replace "k%" with --%--.

UNITED STATES PATENT AND TRADEMARK OFFICE
CERTIFICATE OF CORRECTION

PATENT NO. : 5,753,139
DATED : May 19, 1998
INVENTOR(S) : Wand et al.

It is certified that error appears in the above-identified patent and that said Letters Patent is hereby corrected as shown below:

In claim 7, replace "herein" with --wherein--.
In claim 18, replace "2,5-pyrimidene" with --2,5-pyrimidine--.
In claim 19, remove the "," after "$R_5$".
In claim 32, column 27, line 40, first formula, please replace "$OC_8H_{13}$" with --$OC_6H_{13}$--.
In claim 32, column 27, line 60, fifth formula, please replace "$C_8H_{12}$" with --$C_6H_{12}$--.
In claim 32, column 27, line 65, sixth formula, please replace "$C_8H_{18}O$" with --$C_8H_{16}O$--.
In claim 32, column 28, line 4, seventh formula, please replace "$C_8H_{18}$" with --$C_8H_{16}$-- and replace "$C_6H_{11}$" with --$C_5H_{11}$--.
In claim 32, column 28, line 9, eighth formula, please replace "$OC_8H_{13}$" with --$OC_6H_{13}$--.
In claim 33, column 28, line 60, first formula, please replace "$C_8H_{13}$" with --$C_6H_{13}$--.
In claim 33, column 29, line 15, fourth formula, please replace "$C_8H_{13}$" with --$C_6H_{13}$--.
In claim 33, column 29, line 20, fifth formula, please replace "$C_8H_{13}$" with --$C_6H_{13}$--.
In claim 34, column 29, line 30, first formula, please replace "$OC_8H_{13}$" with --$OC_6H_{13}$--.
In claim 34, column 29, line 50, fifth formula, please replace "$C_8H_{12}$" with --$C_6H_{12}$--.
In claim 34, column 29, line 55, sixth formula, please replace "$C_8H_{18}O$" with --$C_8H_{16}O$--.
In claim 34, column 29, line 60, seventh formula, please replace "$C_8H_{18}$" with --$C_8H_{16}$-- and replace "$C_6H_{11}$" with --$C_5H_{11}$--.
In claim 34, column 29, line 65, eighth formula, please replace "$OC_8H_{13}$" with --$OC_6H_{13}$--.
In the title, replace "FERROELECTRIC PITCH FERROELECTRIC PITCH" with --FERROELECTRIC PITCH--

Column 1, lines 4-5 Title should read --FERROELECTRIC PITCH--.

Signed and Sealed this

Twenty-ninth Day of September, 1998

Attest:

Attesting Officer

BRUCE LEHMAN
Commissioner of Patents and Trademarks